United States Patent [19]

Radzio et al.

[11] Patent Number: 4,986,285

[45] Date of Patent: Jan. 22, 1991

[54] METHOD AND APPARATUS FOR ASCERTAINING THE DENSITY OF WRAPPED TOBACCO FILLERS AND THE LIKE

[75] Inventors: Andrzej Radzio, Quinton, Va.; Wolfgang Stems, Hamburg, Fed. Rep. of Germany

[73] Assignee: Körber AG, Hamburg, Fed. Rep. of Germany

[21] Appl. No.: 279,407

[22] Filed: Dec. 2, 1988

Related U.S. Application Data

[63] Continuation of Ser. No. 837,096, Mar. 6, 1986, Pat. No. 4,805,641, and a continuation-in-part of Ser. No. 760,995, Jul. 31, 1985.

[51] Int. Cl.$^5$ .............................. A24C 5/14; A24C 5/34
[52] U.S. Cl. .................................... 131/280; 131/84.1; 131/905; 131/906; 131/908
[58] Field of Search ...................... 131/84.1, 280, 905, 131/906, 908, 86.1,

[56] References Cited

FOREIGN PATENT DOCUMENTS

| 0759532 | 10/1956 | United Kingdom | 131/84.1 |
| 1044020 | 9/1966 | United Kingdom | 131/84.1 |
| 2133965 | 8/1984 | United Kingdom | 131/84.1 |

*Primary Examiner*—V. Millin
*Attorney, Agent, or Firm*—Peter K. Kontler

[57] ABSTRACT

The density of successive increments of a cigarette rod is measured by an apparatus which employs one or more photocells operating with ultraviolet, infrared or visible light. The radiation source of each photocell emits a beam of ultraviolet, infrared or visible light which penetrates through the wrapper and the filler of the rod and thereupon impinges upon one or more transducers which transmit signals denoting the density of the monitored portion of the rod to an evaluating circuit. The beams which are emitted by two or more discrete radiation sources are or can be angularly offset with reference to each other, and the evaluating circuit processes the signals from the photocells to generate a single signal which is indicative of the density of the monitored increment of the rod and is used to adjust the trimming device and/or the ejector for defective cigarettes.

2 Claims, 6 Drawing Sheets

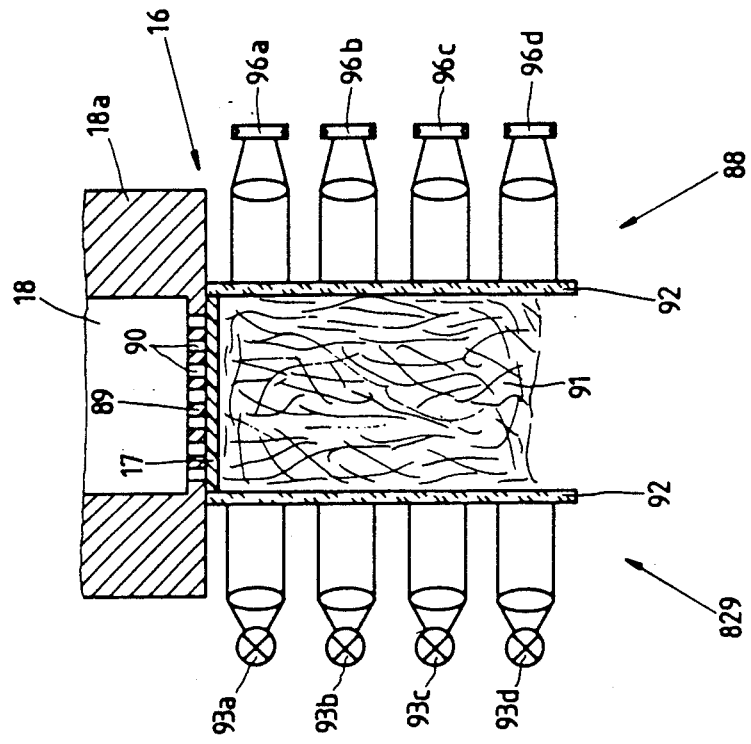
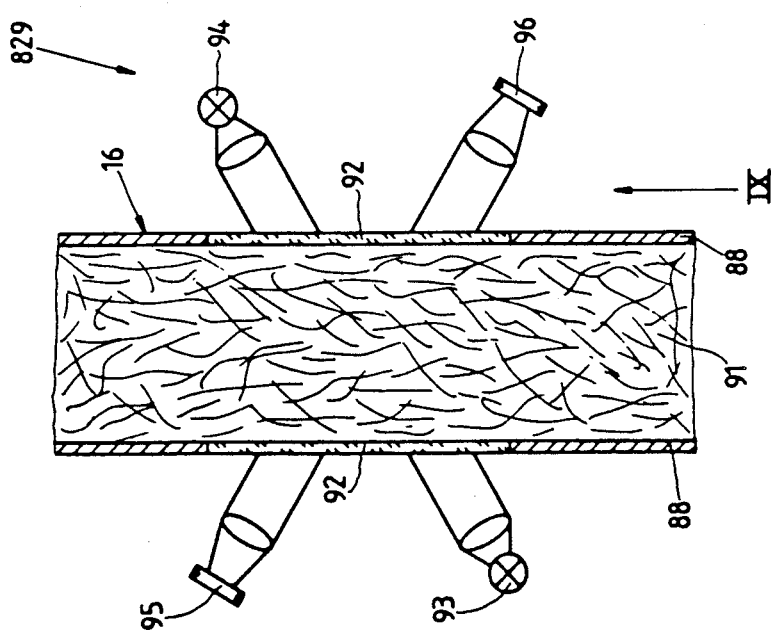
Fig. 9
Fig. 8

METHOD AND APPARATUS FOR ASCERTAINING THE DENSITY OF WRAPPED TOBACCO FILLERS AND THE LIKE

This application is a continuation of application Ser. No. 837,096, filed Mar. 6, 1986, which is a continuation-in-part of Ser. No. 760,995, filed July 31, 1985 now U.S. Pat. No. 4,805,641.

BACKGROUND OF THE INVENTION

The present invention relates to improvements in methods of and apparatus for ascertaining certain characteristics of wrapped or unwrapped tobacco fillers, wrapped or unwrapped fillers of filter material for tobacco smoke and/or similar fillers, rods, streams or analogous bodies which contain a fibrous material. More particularly, the invention relates to improvements in methods of and in apparatus for measuring the density of successive or selected increments of a moving elongated body of fibrous material. Still more particularly, the invention relates to improvements in methods of and in apparatus for measuring the density of successive or selected increments of wrapped or unwrapped fillers of tobacco and/or other fibrous material by means of one or more beams of penetrative radiation.

It is already known to measure the density of successive increments of a wrapped filler of tobacco or the like (hereinafter called cigarette rod with the understanding, however, that the same technique can be relied upon for the testing of all kinds of fibrous materials including fillers which are used for the making of plain and filter cigarettes, cigars, cigarillos and/or filter rod sections) by directing one or more beams of penetrative radiation against the rod so that the intensity of radiation which has penetrated through the rod is a function of the density of the corresponding portion of the rod. The intensity and/or other characteristics of such radiation are monitored subsequent to penetration through the rod, and the signals which are generated by the monitoring means are indicative of the density of the corresponding increment or increments of the rod. In many instances, the means for directing one or more beams of penetrative radiation against the rod is designed to traverse successive increments of the rod within the confines of suitable means for guiding the rod, e.g., a cylindrical sleeve. Signals which are generated by the monitoring means can be processed in a number of different ways, for example, to regulate the density if the monitored density deviates from a desired value, to stop the machine if the difference between the monitored density and the desired density exceeds a preselected threshold value and/or to eject those articles which contain defective portions of the rod.

In accordance with an earlier proposal which is disclosed in commonly owned U.S. Pat. No. 4,424,443, radiation which is caused to penetrate through a rod of fibrous material includes beta rays. It was also proposed to employ X-rays (reference may be had to U.S. Pat. No. 3,056,026 and to commonly owned U.S. patent application Ser. No. 572,563); however, applicants and their assignee are not aware of any cigarette makers or analogous tobacco processing machines which employ density measuring apparatus operating with X-rays. A serious drawback of all presently known apparatus which measure the density of tobacco fillers or the like with beams of penetrative radiation is that the radiation is radioactive which renders it necessary to undertake numerous and highly expensive precautionary measures so as to prevent contamination of the plant and impairment of the health of attendants.

OBJECTS AND SUMMARY OF THE INVENTION

An object of the invention is to provide a novel and improved method of ascertaining the density of bodies of fibrous material without reliance on radioactive and/or other potentially harmful radiation.

Another object of the invention is to provide a method which allows for simple, inexpensive and reproducible determination of the density of successive or selected increments of a continuously or intermittently advancing body of fibrous material, such as a wrapped or unwrapped stream or filler which consists of or contains tobacco particles.

A further object of the invention is to provide a method which can be practiced in existing plants without expensive and complex precautionary measures of the type required when the ascertainment of density of wrapped fillers of tobacco or the like involves the use of beta rays, X-rays or similar radiation.

An additional object of the invention is to provide a method which renders it possible to simultaneously or successively test one and the same portion of a moving body of fibrous material by two or more discrete testing units.

Still another object of the invention is to provide a novel and improved apparatus for the practice of the above outlined method.

A further object of the invention is to provide the apparatus with novel and improved means for initiating the generation of signals which denote the density of selected portions of a wrapped filler of tobacco particles or the like.

Still another object of the invention is to provide novel and improved means for evaluating signals which are generated during ascertainment of the density of selected or successive increments of a running cigarette rod or the like.

Another object of the invention is to provide novel and improved means for emitting beams of radiation in the above outlined apparatus.

A further object of the invention is to provide a cigarette maker which embodies the above outlined apparatus.

An additional object of the invention is to provide a production line for the making of rod-shaped smoker's products which embodies the above outlined apparatus.

One feature of the present invention resides in the provision of a method of ascertaining the density of a body of fibrous material, particularly for ascertaining the density of a wrapped rod-like filler which contains particles of tobacco and/or filter material. The method comprises a first step of directing at least one beam of infrared radiation, ultraviolet radiation or visible light (with a wavelength between approximately 150 and 15,000 nm, preferably infrared radiation with a wavelength of approximately 900 nm) into the body of fibrous material so that the beam penetrates through at least a portion of the body and at least one of its characteristics (e.g., its intensity) is influenced by the density of the body of fibrous material, a second step of monitoring the one characteristic of the beam subsequent to its penetration through at least a portion of the body of fibrous material, and a third step of generating a signal which is indicative of the monitored characteristic of the beam.

In accordance with one presently preferred embodiment of the method, the first step includes directing against the body of fibrous material several mutually inclined beams of radiation, the second step includes individually monitoring the one characteristic of each of the beams subsequent to their penetration through a portion at least of the body of fibrous material, the third step includes generating discrete signals each of which is indicative of the monitored characteristic of a different beam, and such method preferably further comprises the step of converting the discrete signals into a single signal. Such converting step can include totalizing the discrete signals into a combined signal and dividing the combined signal by the total number of beams. The number of discrete beams preferably exceeds two and, if the body has a substantially circular cross-sectional outline, the first step preferably includes directing the beams substantially radially of the body at angles of approximately or exactly 120 degrees to each other.

If the body is elongated, the first step can include directing a plurality of discrete beams of infrared radiation, ultraviolet radiation or visible light substantially radially against longitudinally spaced-apart portions of the body, the second step includes individually monitoring the one characteristic of each of the beams subsequent to penetration of the respective beam through a portion of or through the entire body of fibrous material, and the third step includes generating discrete signals each of which is indicative of the monitored characteristic of a different beam.

The first step can include directing radiation in at least one predetermined direction whereby at least some radiation is reflected and scattered by the fibrous material in the body and such scattered and reflected radiation emerges from the body in at least one second direction at an angle to the predetermined direction. The second step can comprise monitoring at least one characteristic of at least some of the scattered and reflected radiation subsequent to emergence of such radiation from the body. If the body is elongated (e.g., a continuous wrapped or unwrapped stream of tobacco and/or filter material), the second step can include monitoring the scattered and reflected radiation at a plurality of locations which are spaced apart from each other circumferentially of the elongated body.

Another feature of the invention resides in the provision of an apparatus for ascertaining the density of a body of fibrous material, particularly for ascertaining the density of a wrapped rod-like filler which contains particles of tobacco and/or filter material for tobacco smoke. The apparatus comprises a source of infrared radiation, ultraviolet radiation or visible light (namely electromagnetic radiation with a wavelength between approximately 150 and 15,000 nm, preferably infrared radiation with a wavelength of approximately 900 nm) including means for directing at least one beam of such radiation into the body of fibrous material so that the beam penetrates through at least a portion of the body and at least one of its characteristics is thereby influenced by the density of the body of fibrous material, and means for monitoring the one characteristic of the beam subsequent to its emergence from the body of fibrous material including means for generating a signal which is indicative of the monitored characteristic of the beam and at least indirectly of the density of the corresponding portion of the body of fibrous material. Some radiation is reflected by the exterior of the body, and the monitoring means is preferably located outside of the path of propagation of reflected radiation. The body normally or often includes a stream of fibrous material, and the apparatus then preferably further comprises means for transporting the stream along a predetermined path as well as means for guiding the stream in a predetermined portion of the path. The directing means then preferably includes means for directing the beam substantially transversely of the predetermined portion of the path The source can include means for directing a plurality of mutually inclined discrete beams against the predetermined portion of the path. If the stream has a substantially circular cross-sectional outline, the beams are preferably directed toward the predetermined portion of the path substantially radially of that portion of the stream which is located within the confines of the guiding means (the latter can comprise a substantially tubular member). The source can be designed to simultaneously direct a plurality of beams toward spaced apart portions of the stream, as considered in the longitudinal direction of the path. The monitoring means of such apparatus can comprise means for generating discrete signals each of which is indicative of the monitored characteristic of a different beam, and the apparatus preferably further comprises means for evaluating the discrete signals. The transporting means of such apparatus preferably comprises means for conveying the stream in a predetermined direction at a predetermined (preferably variable) speed, and the signal generating means then preferably includes a series of optoelectronic transducers, one for each of the beams, and the transducers of such series are arranged to transmit to the evaluating means signals one after the other at intervals whose duration is a function of the speed of the stream and of mutual spacing of the aforementioned longitudinally spaced apart portions of the stream.

The evaluating means can comprise means for totalizing the discrete signals which are generated by several transducers, means for amplifying the discrete signals prior to totalizing, and means for dividing the totalized signal by the number of discrete beams (i.e., for averaging the signals from discrete transducers).

The apparatus can further comprise means for influencing the source of electromagnetic radiation, and such influencing means comprises means for generating reference signals which denote at least one characteristic (e.g., the intensity) of selected radiation at least a portion of which does not penetrate through the body of fibrous material, and means for transmitting such reference signals to the source, e.g., to a source of electrical energy which forms part of the source of ultraviolet radiation, visible light or infrared radiation. The reference signals can be used to influence the intensity of radiation issuing from the source.

The influencing means can include a discrete source which is arranged to direct an additional beam of radiation along a discrete path which bypasses the body of fibrous material, and the means for generating reference signals then preferably includes one or more photoelectronic transducers which monitor the one characteristic of the additional beam. Alternatively, the source of infrared radiation, ultraviolet radiation or visible light includes means for directing an additional beam of such radiation against the body of fibrous material in such a way that the body reflects at least a portion of the additional beam. The means for generating reference signals then includes one or more photoelectronic transducers which generate signals denoting at least one characteristic of the reflected portion of the additional beam.

The influencing means can include means for maintaining the intensity of infrared radiation, ultraviolet radiation or visible light issuing from the source at a predetermined value. Alternatively, the apparatus can comprise or further comprises means for modifying the signal which is indicative of the monitored characteristic of the beam or beams of selected radiation in response to deviation of the one characteristic of the reference signal from a predetermined value which denotes a predetermined intensity of selected radiation issuing from the source (i.e., the reference signal is then used as a means for correcting the signals denoting the density of the body of fibrous material in response to detection that the intensity of selected radiation issuing from the source is above or below a preselected optimum value).

As mentioned above, the wavelength of electromagnetic radiation is preferably between about 150 to 15,000 nm. For example, the radiation is infrared radiation with a wavelength of approximately 900 nm. Such infrared radiation can be emitted by one or more diodes.

If the body is a stream of fibrous material (e.g., a wrapped or unwrapped tobacco stream which is processed in a cigarette maker), the exterior of the stream reflects some of the radiation. The means for transporting the stream along a predetermined path includes the aforementioned means for guiding the stream along a predetermined portion of the path, and such guiding means is preferably permeable to electromagnetic radiation which is used to ascertain the density and/or another characteristic of the stream. The directing means can include means for directing a plurality of discrete beams against the predetermined portion of the path, and the monitoring means can include a plurality of means for generating discrete signals each of which is indicative of the monitored characteristic of radiation that has passed through a portion of or through the entire stream. The signal generating means is preferably located outside of the path of propagation of radiation which is reflected by the exterior of the stream.

The directing means can include at least one pair of radiation sources which are disposed substantially diametrically opposite each other with reference to the predetermined path. Analogously, the means for generating signals can include at least one pair of signal generators which alternate with the pair of radiation sources and are disposed substantially diametrically opposite each other with reference to the predetermined path.

In accordance with another embodiment of the invention, the directing means can include at least one radiation source which directs one or more beams of radiation toward the stream at an oblique angle to the longitudinal direction of the stream, and the monitoring means then includes at least one optoelectronic transducer which is disposed in the path of radiation that has penetrated through a portion of or through the entire stream and is located outside of the path of propagation of radiation which is reflected at the exterior of the stream.

The just described apparatus preferably further comprises means for intercepting (e.g., absorbing) reflected radiation between the directing means and the monitoring means to thus reduce the likelihood of impingement of reflected radiation upon the photoelectronic transducer or transducers of the monitoring means.

The body can constitute or include an unwrapped stream of fibrous material which is processed in a cigarette maker. As mentioned above, the guiding means of the transporting means is preferably permeable to the selected electromagnetic radiation, and the directing means then includes one or more sources of radiation which direct one or more beams of radiation toward the unwrapped stream through the guiding means. Such beam is normally partly reflected and partly scattered by fibrous material in the stream, and the monitoring means preferably includes means for ascertaining the one characteristic of scattered and reflected radiation. The directing means of such apparatus can include a plurality of radiation sources which are spaced apart from one another transversely of the stream, and the monitoring means of such apparatus can include a plurality of photoelectronic transducers which are also spaced apart from one another transversely (i.e., rather than longitudinally) of the stream.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 8 is an enlarged fragmentary longitudinal sectional view of still another density measuring apparatus; and FIG. 9 is a view as seen in the direction of arrow IX in FIG. 8.

DESCRIPTION OF THE PREFERRED EMBODIMENTS

Figure 1:
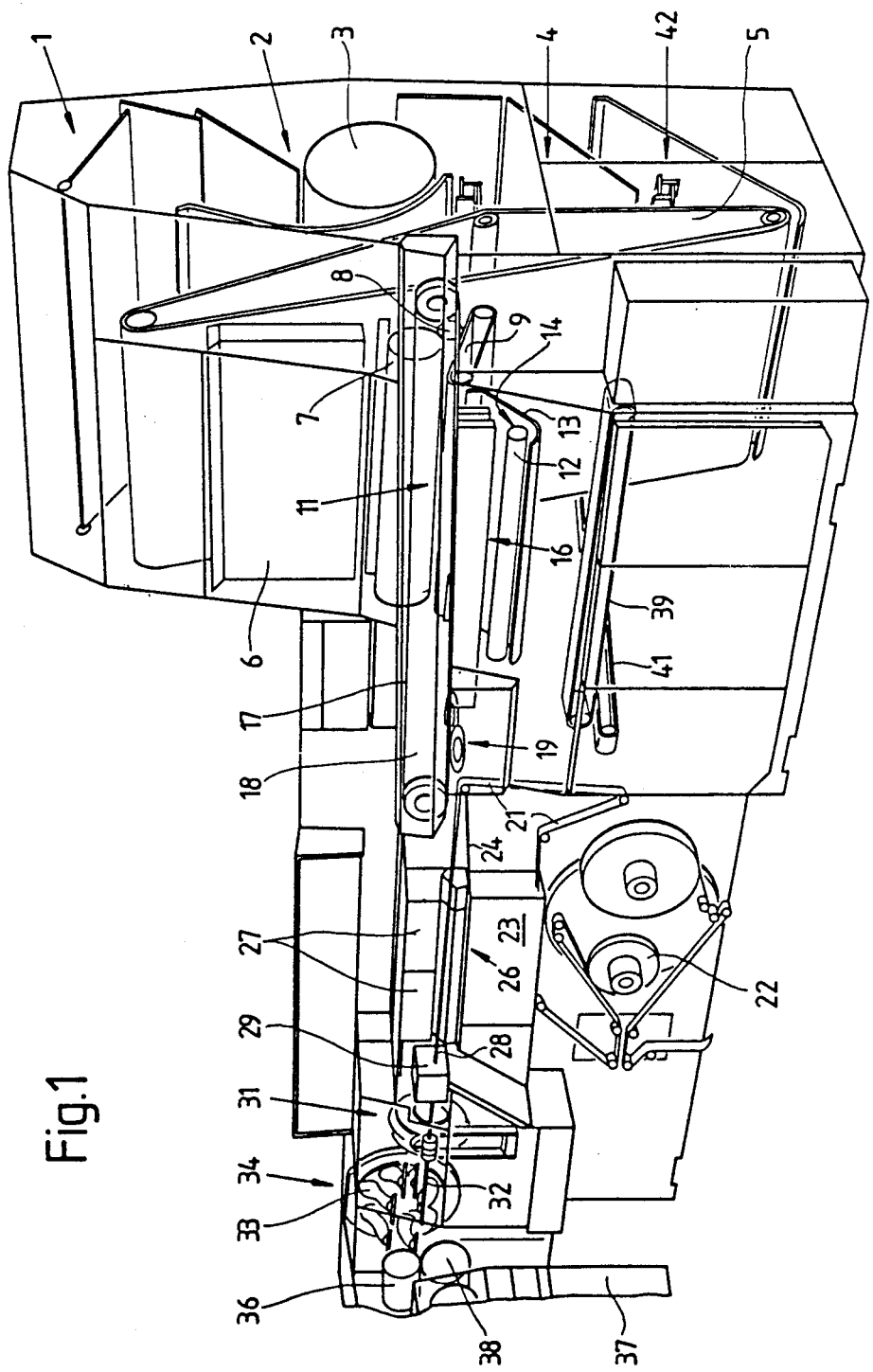
FIG. 1 is a perspective view of a cigarette maker comprising a density measuring apparatus which embodies one form of the present invention.

Referring first to FIG. 1, there is shown a cigarette rod making machine which embodies one form of the improved density measuring apparatus. The machine is of the type known as PROTOS (manufactured and sold by the assignee of the present application) and comprises a gate 1 which is opened at required intervals in order to deliver batches of comminuted tobacco leaves into a first magazine 2. The latter is adjacent to a drum-shaped tobacco removing conveyor 3 which delivers particles of tobacco into a second magazine 4 so that the magazine 4 contains a substantially constant supply of fibrous material. The magazine 4 is adjacent to the upwardly advancing reach of an elevator in the form of a steep belt or chain conveyor 5 which is provided with spaced-apart pockets for transport of relatively small batches of tobacco particles into the inlet of an upright duct 6. The outlet at the lower end of the duct 6 is adjacent to a rotary drum-shaped conveyor 7 which is provided with a peripheral carding serving to advance a continuous and homogeneous layer of tobacco particles into the range of a rapidly driven picker roller 8. The latter expels the particles from the carding of the conveyor 7 and propels them onto the upper reach of a relatively wide belt conveyor 9 whereon the particles accumulate into a wide carpet successive increments of which are advanced into the range of a pneumatic classifying device 11 which defines a curtain of substantially vertical air streams. The inertia of heavier particles (such as fragments of tobacco ribs and the like) suffices to ensure that the trajectories of such particles are not appreciably affected by the curtain of air streams so that the heavier particles are free to enter a suitable collecting receptacle. The inertia of the remaining (satisfactory) particles is relatively low; therefore, the air curtain deflects such particles (mainly shreds of tobacco leaf laminae) into a funnel 14 which is defined by a driven carded drum 12 and a suitably configured wall 13. The carding of the drum 12 entrains the lighter particles through the funnel 14 and propels the thus entrained particles into a tobacco channel 16 wherein the particles rise by suction to accumulate at the underside of the lower reach of an elongated foraminous tobacco stream forming belt conveyor 17. The upper side of the lower reach of the conveyor 17 is adjacent to the at least partially open underside of a suction chamber 18 which causes the ascending particles of tobacco to form a growing tobacco stream which is advanced toward and past a suitable trimming or equalizing device 19 serving to remove the surplus from the thus obtained tobacco stream and to convert the trimmed tobacco stream into a filler which is transferred onto the upper side of a continuous web 21 of cigarette paper supplied by a reel 22 mounted at the front side of the frame of the cigarette rod making machine. The web 21 is advanced in the direction of longitudinal movement of the tobacco filler by the upper reach of an endless belt conveyor 24, and successive increments of the web 21 are caused to pass through a conventional imprinting device 23 on their way toward the upper reach of the conveyor 24. The latter advances successive increments of the web 21 and successive increments of the filler through a wrapping mechanism 26 wherein the web is draped around the filler in such a way that one marginal portion of the web extends substantially tangentially of and away from the filler. The projecting marginal portion is then coated with one or more films of adhesive paste which is supplied by a conventional paster, and the thus coated marginal portion is folded over the other marginal portion to form therewith a seam which extends in parallelism with the axis of the resulting continuous cigarette rod 28. The seam is cooled or heated by the plates of a tandem sealer 27 (depending upon the nature of the adhesive which is used in the seam) so that the seam is less likely to open during travel through a cutoff 31 wherein the rod 28 is subdivided into sections (plain cigarettes) of unit length or multiple unit length. The cutoff 31 is located upstream of a density measuring apparatus 29 which is constructed and operates in accordance with one feature of the present invention. The signals which are transmitted by the density measuring apparatus 29 are utilized to adjust the position of the trimming device 19 with reference to the underside of the lower reach of the conveyor 17 and to thus alter the density of the filler if the monitored density deviates from an optimum value.

The cutoff 31 in the machine of FIG. 1 is designed to subdivide the rod 28 into plain cigarettes 32 of double unit length. Successive cigarettes 32 are engaged by successive orbiting arms 33 of a transfer conveyor 34 and are inserted into or deposited in successive axially parallel peripheral flutes of a drum-shaped conveyor 36 forming part of a filter tipping machine 37, e.g., a machine of the type known as MAX or MAX S (both manufactured and distributed by the assignee of the present application). The conveyor 36 delivers successive plain cigarettes 32 into the flutes of a severing drum 38 which cooperates with a suitable circular disc-shaped knife to subdivide each cigarette 32 into a pair of coaxial plain cigarettes of unit length. The plain cigarettes of each pair are moved axially of and away from each other to provide room for a filter mouthpiece of double unit length. Such mouthpiece is secured to the respective pair of plain cigarettes of unit length by a suitable uniting band consisting of tipping paper and serving to convert the plain cigarettes and the mouthpiece into a filter cigarette of double unit length.

The cigarette rod making machine of FIG. 1 further comprises two endless belt conveyors 39 and 41 which serve to deliver the surplus from the station for the trimming device 18 to a third magazine 42 which is disposed at a level below the second magazine 4 and serves to admit small batches of returned tobacco particles into successive pockets of the conveyor 5. Each such pocket thereupon receives tobacco particles from the magazine 4 before its contents are dumped into the duct 6.

Figure 2:
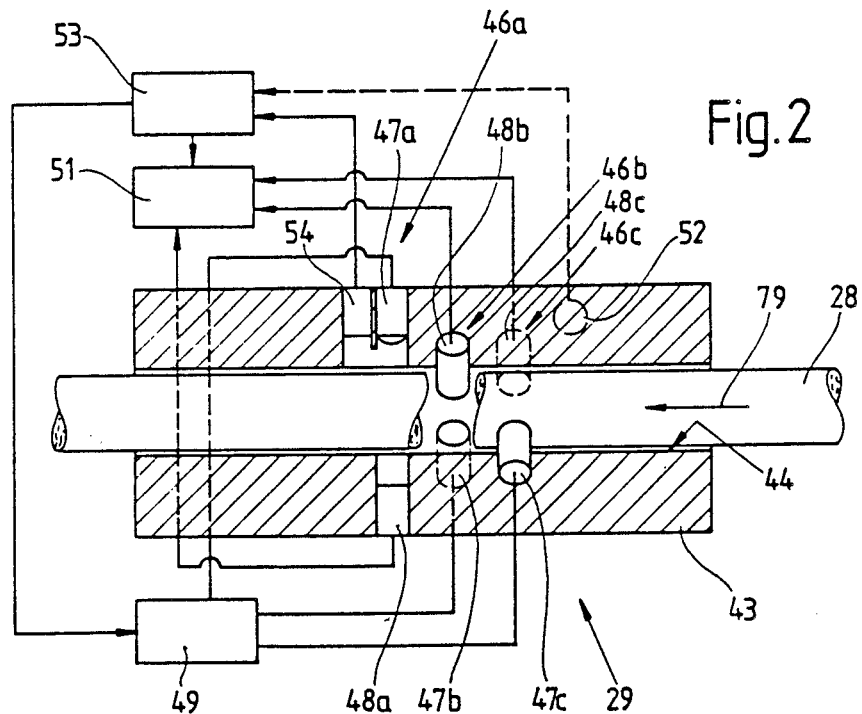
FIG. 2 is an enlarged partly sectional and partly diagrammatic view of the density measuring apparatus.

As shown in FIG. 2, the density measuring apparatus 29 comprises a tubular member 43 which constitutes a means for guiding the cigarette rod 28 along a predetermined portion of an elongated path the major portion of which is defined by the aforementioned conveyor 24 constituting the means for transporting the rod 28 longitudinally toward the cutoff 31. The tubular member 43 (hereinafter called sleeve for short) has an axially extending passage 44 (e.g., a cylindrical bore) for successive increments of the rod 28. The sleeve 43 is formed with radially extending bores for portions of three photocells 46a, 46b, 46c. These photocells respectively comprise sources 47a, 47b, 47c of infrared light and photoelectronic transducers 48a, 48b, 48c which are disposed diametrically opposite the corresponding sources with reference to the axis of the sleeve 43. The transducers 48a, 48b, 48c are designed to generate signals denoting the intensity of those portions of the beams of infrared light which have issued from the respective sources 47a, 47b, 47c and have penetrated substantially diametrically through the corresponding portions of the rod 28 in the passage 44. The beams of infrared radiation travel substantially radially of the rod 28 and their intensities and/or other characteristics are influenced by the density of those portions of the filler of the rod 28 which happen to be located between the sources 47a–47c and the respective transducers 48a–48c.

Figure 3:
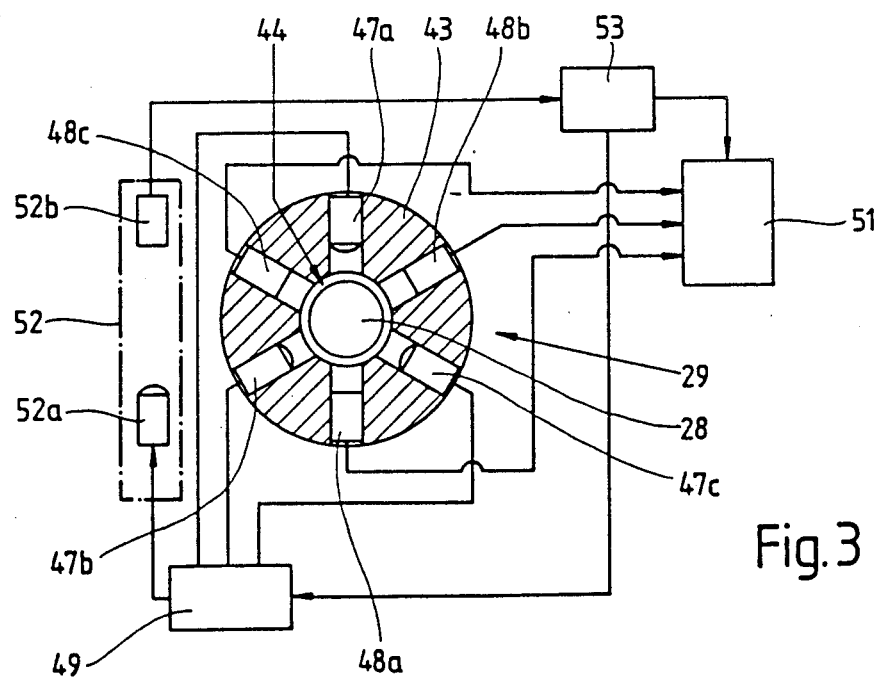
FIG. 3 is a partly transverse sectional and partly diagrammatic view of a modified density measuring apparatus.

The sources 47a–47c and the transducers 48a–48c are angularly offset with reference to each other by 120 degrees, as considered in the circumferential direction of the rod 28 (see FIG. 3). As shown in FIG. 2, the photocells 46a, 46b, 46c can be spaced apart from one another, as considered in the longitudinal direction of the rod 28 in the passage 44 of the sleeve 43. The embodiment of FIG. 3 differs from that of FIG. 2 in that all three photocells of the density measuring apparatus of FIG. 3 are located in a common plane which is disposed at right angles to the axis of the passage 44 The apparatus of FIG. 3 can be utilized with advantage to ascertain the density of successive increments of a rod 28 which is transported at a relatively low speed The apparatus of FIG. 2 (with the photocells 46a–46c staggered relative to each other as considered in the axial direction of the passage 44) is preferred for use in machines wherein the rod 28 is transported at an elevated speed, e.g., in a modern cigarette maker which turns out up to and in excess of 8000 cigarettes per minute. The arrangement is then preferably such that the series of three successive photoelectronic transducers 48a, 48b, 48c is arranged to monitor the characteristics of beams of infrared radiation which have passed through one and the same increment of the moving rod 28, i.e., that such increment is first traversed by the beam which is monitored by the rearmost transducer 48c, that such increment is thereupon traversed by the beam which is monitored by the median transducer 48b, and that the same increment is ultimately traversed by the beam which is monitored by the foremost or leftmost transducer 48a of FIG. 2. Thus, each increment is tested thrice, each time by a different photocell and each time by passing therethrough a beam of infrared radiation at an angle of approximately or exactly 120 degrees with reference to the preceding beam.

The sources 47a–47c are connected to a common source 49 of electrical energy, and the outputs of the transducers 48a–48c are connected to a common evaluating circuit 51 which processes the signals denoting the selected characteristics of the three beams of infrared radiation after such beams have passed through an increment of the moving cigarette rod 28. The sources 47a–47c and the energy source 49 can be said to constitute a composite source of infrared radiation for all three photoelectronic transducers 48a–48c.

FIG. 3 shows an additional photocell 52 which constitutes part of a means for influencing the composite source 47a–47c, 49 of infrared radiation and includes a source 52a of infrared radiation and a photoelectronic transducer 52b. The source 52a is connected to the energy source 49 and emits a beam of infrared radiation at least a portion of which bypasses the path of the cigarette rod 28. The output of the transducer 52b transmits signals which are converted into reference signals by a circuit 53 whose output is connected to one input of the evaluating circuit 51 as well as to the energy source 49, i.e., the reference signal can influence the energy source 49 when the intensity of the reference signal which is furnished by the circuit 53 deviates from a preselected value. FIG. 2 shows one presently preferred position of the photocell 52 by broken lines.

The photocell 52 can be used in addition to or in lieu of a further photocell including one of the sources 47a, 47b, 47c of infrared radiation and a photoelectronic transducer 54. The latter transmits signals to the circuit 53 which transmits reference signals to the evaluating circuit 51 and to the energy source 49. Some of the radiation which issues from one of the sources 47a–47c (namely from the source 47a of FIG. 2) is reflected by the external surface of the wrapper of the rod 28 and impinges upon the photoelectronic transducer 54 so that the latter monitors a characteristic of infrared radiation which was emitted by the source 47a but did not penetrate through the rod 28. The signals which are generated by the transducer 54 and are converted into reference signals by the circuit 53 can be used to influence the composite source 49, 47a–47c as well as to enable the evaluating circuit 51 to properly process the signals which are transmitted by the transducers 48a–48c.

Figure 4:
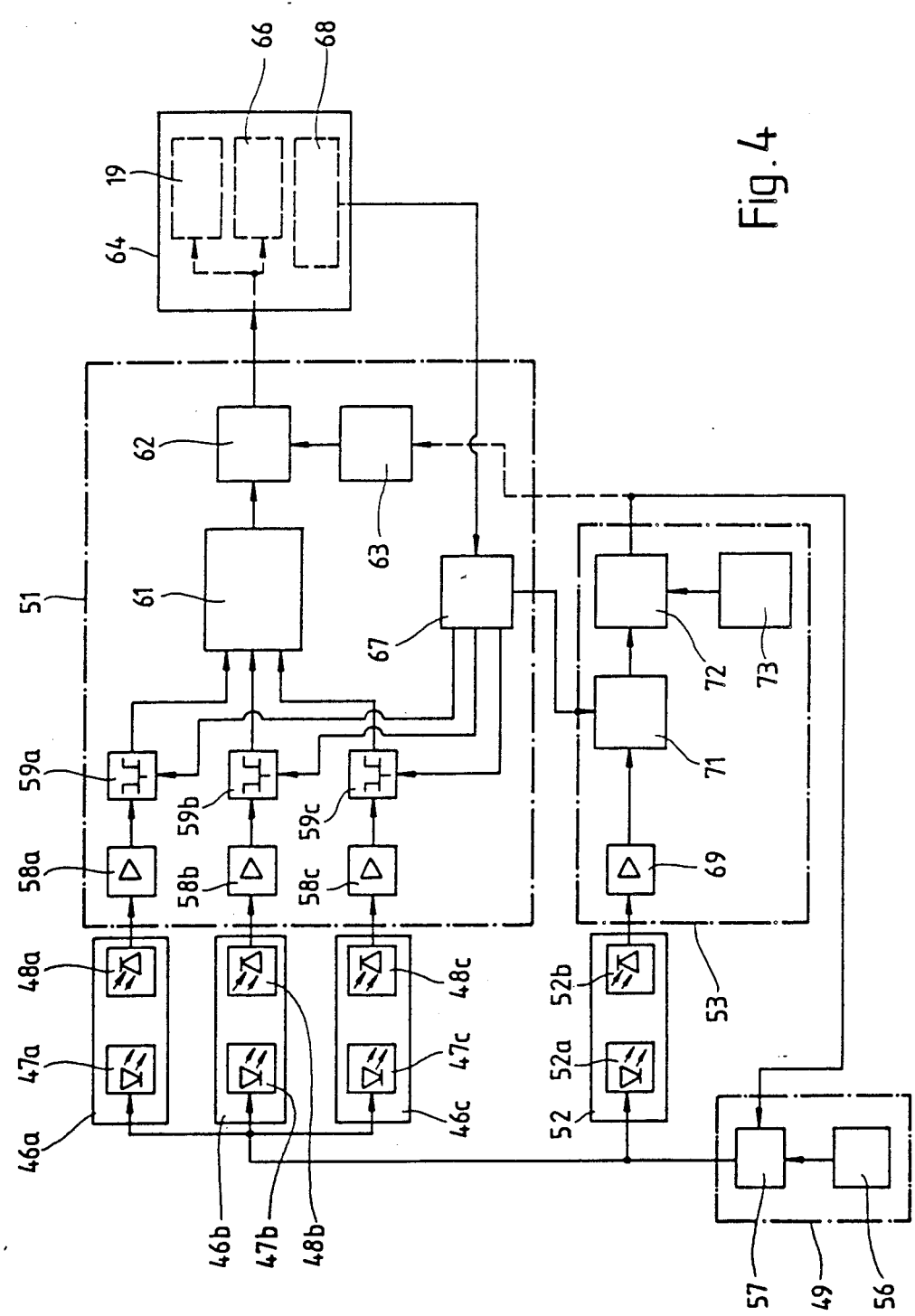
FIG. 4 is a block diagram of the density measuring apparatus as well as of the parts which are influenced by signals denoting the ascertained density of successive increments of a running cigarette rod.

FIG. 4 shows the details of a density measuring apparatus of the type described with reference to FIGS. 2 and 3. The composite source of infrared radiation includes a source 49 of electrical energy and three discrete sources 47a, 47b, 47c of beams of infrared radiation. These discrete sources form part of three photocells 46a, 46b, 46c which further comprise photoelectronic transducers 48a, 48b, 48c. The inputs of the discrete sources 47a–47c are connected to the output of the energy source 49, the same as the input of a source 52a which forms part of the additional photocell 52. The latter further includes a transducer 52b which transmits signals to the circuit 53 for generation of reference signals which influence the energy source 49. The source 49 includes a source 56 of potential and a regulator 57 which is designed to maintain the intensity of current at a constant value. Such design of the energy source 49 ensures that the intensity of beams of infrared radiation which are emitted by the sources 47a, 47b, 47c remains constant or fluctuates only negligibly when the cigarette maker 64 of FIG. 1 is in use.

The outputs of the transducers 48a, 48b, 48c are respectively connected to the inputs of amplifiers 58a, 58b, 58c which form part of the evaluating circuit 51 and are connected in series with switching elements 59a, 59b, 59c, respectively. The outputs of the switching elements 59a–59c are connected with the corresponding inputs of an averaging circuit 61 which also forms part of the evaluating circuit 51 and includes means for totalizing the three signals and for thereupon dividing the resulting signal with the total number of beams of infrared radiation so that the output of the circuit 61 transmits an averaged signal which is indicative of the density of the corresponding thrice monitored increment or section of the rod 28.

Due to exponential relationship between the density d of the rod and intensity of radiation which passes through the rod, it is preferred to logarithmize the signals, either prior to totalizing or in the course of signal processing. The relationship between the density d and the intensity of radiation can be expressed by the equation $d \sim \log J \cdot J_D/J_o$ wherein J is the intensity of the signal, $J_D$ is the dark current of the transducer and $J_o$ is the intensity of the primary beam. The signals can be individually amplified and logarithmized; to this end, the amplifiers 58a–c and 69 can constitute logarithmic amplifiers, e.g., type ICL 8048 manufactured by Intersil. Alternatively, the logarithms of measurement signals can h=stored in a memory which is addressed for further processing of memorized signals when necessary. The memory or memories can be installed ahead of or downstream of the respective amplifiers and are not specifically shown in the drawing. The utilization of such memories is well known to artisans possessing the requisite skill in this field.

The block diagram of FIG. 4 (this also applies for the block diagram of FIG. 5) shows the circuit in a schematic form for the sake of convenience and simplicity. In actual practice, e.g., in a cigarette maker, the evaluating circuit preferably comprises a computer wherein the aforediscussed parts do not constitute discrete elements but the computer performs the aforedescribed logarithmizing and other evaluating operations with the same result. are transmitted by the output of the circuit 63, and the signals from the comparator circuit 62 are used to influence the operation of the cigarette maker 64, particularly to influence the position of the trimming device 19 with reference to the lower reach of the conveyor 17 and to thereby influence the density of the filler of the rod 28 by causing the device 19 to remove a larger or a smaller quantity of surplus tobacco and/or to actuate an ejector 66 (e.g., a nozzle which discharges blasts of compressed air) serving to segregate defective plain cigarettes 32 from satisfactory cigarettes ahead of the filter tipping machine 37. The signal which denotes the density of the filler of the rod 28 can also influence other parts of the cigarette maker 64, i.e., any parts which can contribute to a change in the density of the filler if such density deviates from an optimum value as well as any parts which can prevent unsatisfactory plain cigarettes from reaching the consumer or the next processing station.

A timer 67 is provided to transmit signals at a frequency which is determined by a timing pulse generator 68 in the cigarette maker 64. The frequency of pulses which are transmitted by the pulse generator 68 is a function of the speed of axial movement of the cigarette rod 28. The signals at the output of the timer 67 are used to activate and deactivate the switching elements 59a–59c, i.e., to permit or prevent the transmission of signals from the outputs of the transducers 58a–58c to the corresponding inputs of the averaging circuit 61. If the sources 47a–47c are located in a common plane which extends at right angles to the axis of the passage 44 in the sleeve 43 (see FIG. 3), the signal at the output of the timer 67 will effect simultaneous activation of all three switching elements 59a–59c, i.e., simultaneous transmission of signals from the outputs of the transducers 58a–58c to the corresponding inputs of the averaging circuit 61. This means that the circuit 61 simultaneously receives three signals each of which is indicative of the density of one and the same increment of the rod 28 as determined by the corresponding beam of infrared light (issuing from the source 47a or 47b or 47c). The circuit 61 then averages the thus obtained signals by totalizing them and by thereupon dividing the resulting signal by three (the total number of beams of infrared radiation) so that the averaged signal which is transmitted to the comparator circuit 62 denotes the average density of the monitored increment of the rod 28 and more particularly of the monitored increment of the rod-like filler in such rod. The comparator circuit 62 compares the averaged signal which is furnished by the averaging circuit 61 with the signal which is transmitted by the circuit 63 (such signal denotes the desired density of successive increments of the filler).

In order to reduce the likelihood of mutual influencing of the photocells 46a–46c, the circuit arrangement of FIG. 4 can be designed in such a way that the timer 67 actuates the switching elements 59a, 59b, 59c one after the other, i.e., the averaging circuit 61 then receives three signals at timely spaced intervals; such signals are totalized and the resulting signal is divided by three to yield a signal which is indicative of average density of the monitored increment of the filler in the cigarette rod 28. If the speed of axial movement of the rod 28 is relatively low and if the switching elements 59a, 59b, 59c are activated immediately or rapidly one after the other, the signal at the output of the circuit 61 adequately denotes the average density of the monitored increment of the filler. This holds true even if the three photocels 46a–46c are disposed in a common plane as shown in FIG. 3. If the density measuring apparatus is incorporated in a modern high-speed cigarette maker, the three photocells 46a–46c are preferably spaced apart from each other, as considered in the longitudinal direction of the filler in the rod 28, i.e., in a manner as shown in FIG. 2.

In order to even further reduce the likelihood of mutual interference of the photocells 46a–46c, it is possible to establish the connections between the energy source 49 and the sources 47a–47c of beams of infrared radiation one after the other in synchronism with activation of the respective switching elements 59a–59c. In other words, the source 47a transmits a beam of infrared light toward and through the adjacent portion of the filler of the rod 28 while the sources 47b, 47c are prevented from transmitting beams of infrared radiation, the source 47b transmits a beam when the sources 47a, 47c are prevented from transmitting beams of infrared radiation toward the respective transducers 48a, 48c, and so on. This will be explained with reference to FIG. 5. Of course, the sources 47a–47c should be activated in such sequence that they transmit beams of infrared radiation through one and the same increment of the filler of the rod 28. This ensures that the averaged signal which is transmitted by the circuit 61 is indicative of the average density of a thrice illuminated increment of the filler.

The additional photocell 52 regulates the intensity of radiation which is furnished by the sources 47a–47c. The output of the transducer 52b of the photocell 52 is connected with an amplifier 69 of the circuit 53 which supplies reference signals to the regulator 57 for the source 56. The output of the amplifier 69 transmits signals to a sample and hold circuit 71 whose output is connected with a signal comparing stage 72. A source 73 of reference signals is provided to supply such signals to the signal comparing stage 72, and the latter transmits a signal when the characteristics of signals from the sample and hold circuit 71 deviate from those which are supplied by the source 73. The regulator 57 then adjusts the source 56 so as to change the intensity of radiation which is emitted by the sources 47a, 47b, 47c. The circuit 53 ensures that the intensity of radiation which is emitted by the sources 47a–47c remains at least substantially constant.

Instead of or in addition to influencing the regulator 57, the signals at the output of the signal comparing stage 72 can be transmitted to the circuit 63 via conductor means which is indicated in FIG. 4 by a broken line Signals which are transmitted by the stage 72 are then used to modify the signals which are transmitted by the comparator circuit 62 so that the signals which are transmitted to the trimming device 19 and to the ejector 66 are influenced by deviations of the intensity of radiation issuing from the sources 47a–47c from an optimum or selected value. In other words, the apparatus is then in a position to compensate for eventual fluctuations of intensity of the radiation which is emitted by the sources 47a–47c.

Figure 5:
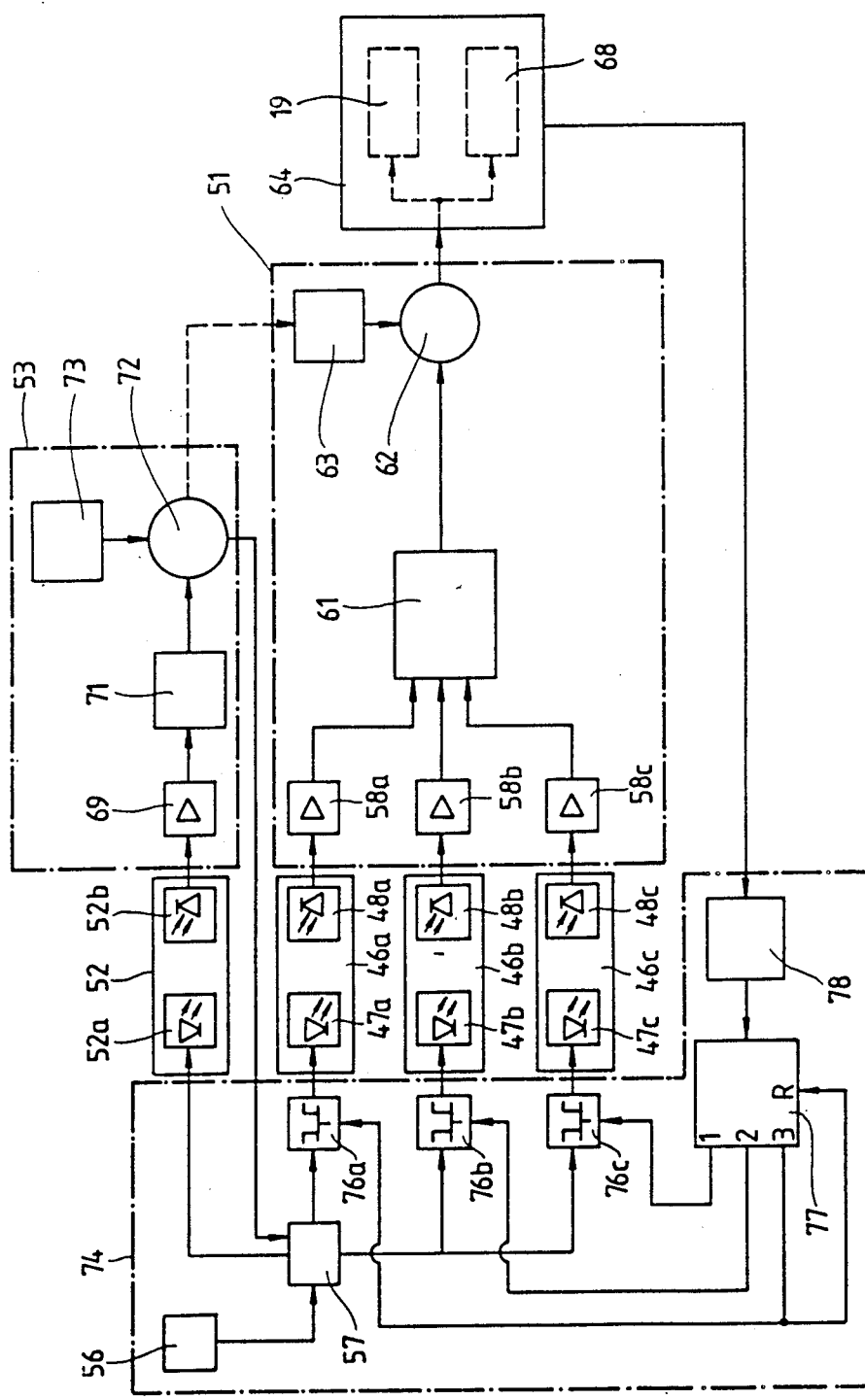
FIG. 5 is a similar block diagram of an apparatus having modified means for evaluating the signals which are indicative of monitored characteristics of several discrete beams of infrared radiation, ultraviolet radiation or visible light.

FIG. 5 shows a modified density measuring apparatus. All such parts of this apparatus which are identical with or clearly analogous to those of the apparatus of FIG. 4 are denoted by similar reference characters The construction of the photocells 46a–46c and 52 is the same as in the apparatus of FIG. 4. The outputs of the transducers 48a–48c are connected with an evaluating circuit 51 whose construction deviates from that of the evaluating circuit of FIG. 4 because it does not contain any switching elements (corresponding to the elements 59a–59c of FIG. 4). Thus, the outputs of the amplifiers 58a–58c are directly connected to the corresponding inputs of the averaging circuit 61 whose output is connected with the comparator circuit 62. The signals which appear at the output of the circuit 62 are transmitted to the parts 19 and 68 of the cigarette maker 64.

The output of the transducer 52b forming part of the photocell 52 is connected to the input amplifier 69 of the circuit 53 which is identical with or similar to the circuit 53 of FIG. 4.

In contrast to the operation of the apparatus of FIG. 4, the apparatus of FIG. 5 is designed to ensure that the sources 47a, 47b, 47c can emit beams of infrared light at intervals which are determined by a counter 77 in dependency on the speed of the rod 28 in the cigarette maker 64. Thus, whereas the apparatus of FIG. 4 comprises means for transmitting signals from the transducers 48a–48c at timely spaced intervals, the apparatus of FIG. 5 causes the sources 47a–47c to emit beams of infrared radiation at timely spaced intervals. To this end, the source 49 of electrical energy which is used in the apparatus of FIG. 4 is replaced with a modified source 74 which also includes a source 56 of potential and a regulator 57 but further includes the aforementioned counter 77, a timing pulse generator 78 which transmits pulses to the counter 77, as well as three switching elements 76a, 76b, 76c which are connected between the output of the counter 77 and the corresponding inputs of the sources 47a, 47b, 47c, respectively.

The timing pulse generator 78 transmits pulses at a frequency which is a function of the speed of the rod 28 in the cigarette maker 64. The first signal which the counter 77 receives is transmitted by its output "1" to actuate the switching element 76c so that the source 47c receives electrical energy and emits a beam of infrared radiation through the adjacent portion of the filler of the rod 28 in a direction toward the associated transducer 48c. The latter generates a signal which is indicative of a characteristic of the beam, namely of a characteristic which denotes the density of the freshly traversed portion of the filler, and such signal reaches the averaging circuit 61 of the evaluating circuit 51 by way of the corresponding amplifier 58c. In the meantime, the rod 28 continues to advance in the direction of arrow 79 (FIG. 2) and, when the aforediscussed portion of the filler reaches the space between the source 47b and the transducer 48b (namely when such space is occupied by that portion of the filler which was previously traversed by the beam of infrared radiation emitted by the source 47c), the output "2" of the counter 77 transmits a signal to the switching element 76b which establishes a connection between the regulator 57 of the source 74 and the source 47b so that the source 47b emits a beam of infrared radiation which impinges upon the transducer 48b and the latter transmits a corresponding signal to the averaging circuit 61 via amplifier 58b. The twice tested portion of the filler of the rod 28 continues to advance in the direction of arrow 79 and reaches the space between the source 46a and transducer 48a when the switching element 76a receives a signal from the output "3" of the counter 77 so that the source 46a then emits a beam of infrared radiation which reaches the transducer 48a after having penetrated diametrically through the filler whereby the transducer 48a generates a corresponding signal which is transmitted to the averaging circuit 61 via amplifier 58a. The output "3" of the counter 77 is connected to the latter's resetting input "R" so that the counter is reset to zero and can proceed with renewed transmission of signals by way of its outputs "1", "2" and "3".

The signal at the output of the circuit 61 denotes the average density of the thrice tested portion of the filler and is transmitted to the comparator circuit 62 where it is compared with the signal from the circuit 63. The circuit 62 transmits a signal to the trimming device 19 and/or to other parts of the cigarette maker 64 whenever the intensity or another characteristic of the signal at the output of the averaging circuit 61 deviates from the same characteristic of the signal which is transmitted by the circuit 63. It will be noted that the evaluating circuit 51 transmits a single signal in response to repeated testing of one and the same increment of the filler which forms part of the rod 28.

FIGS. 2 to 5 illustrate density measuring apparatus which employ infrared light. Each source of infrared light can constitute a diode which emits radiation having a wavelength of approximately 900 nm. Such radiation is particularly advantageous for density measurement because the moisture content of tobacco and/or other fibrous material of the tobacco processing industry exerts a minimal (practically negligible) influence upon the results of the monitoring operation which involves detection of one or more characteristics of infrared light in the range of 900 nm. Consequently, it is not necessary to equip the density measuring apparatus with means for correcting the signals so as to compensate for the fluctuations of the moisture content of fibrous material.

Figure 6:
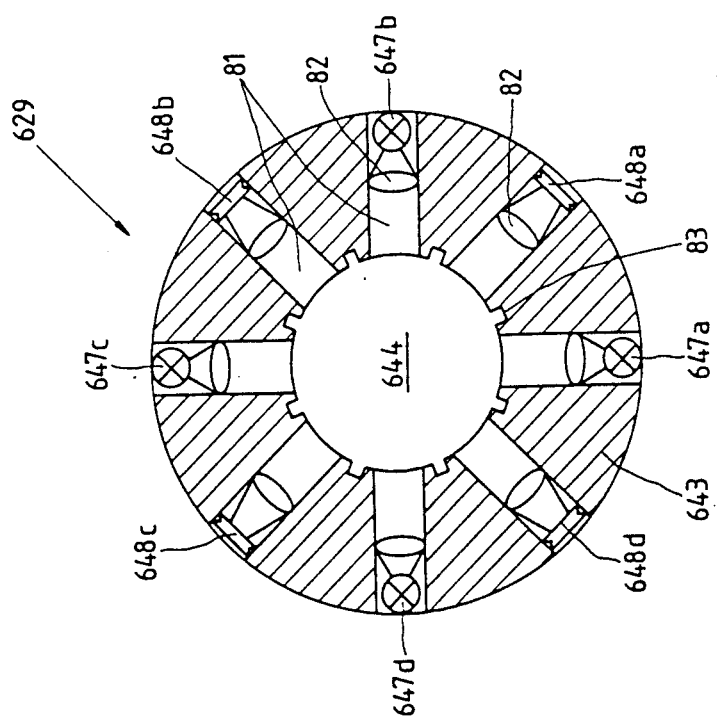
FIG. 6 is an enlarged fragmentary transverse sectional view of a further density measuring apparatus.

Another presently preferred embodiment of the improved density measuring apparatus is shown in FIG. 6. The apparatus 629 of FIG. 6 having a sleeve 643 with an axial bore 644 for the wrapped or unwrapped stream of fibrous material (not shown), and an annulus of eight equidistant coplanar substantially radially extending bores or holes 81 which communicate with the axial bore 644. Alternate bores 81 contain discrete radiation sources 647a, 647b, 647c and 647d, and the remaining bores 81 contain discrete monitoring devices (e.g., photoelectronic transducers) 648a, 648b, 648c and 648d. In order to enhance predictable propagation of beams of radiation from the sources 647a–647d toward the body of fibrous material in the bore 644 and from such body toward the monitoring devices 648a–648d, the radial bores 81 preferably contain optical elements in the form of lenses 82 or the like.

The radiation sources 647a and 647c constitute a first pair of radiation directing means which are disposed diametrically opposite each other with reference to the body of fibrous material in the bore 644. The same applies for the pair of radiation sources 647b, 647d. Thus, such radiation sources are not in the embodiments of FIGS. 2 and 3. The monitoring devices 648a, 648c constitute a first pair of photoelectronic transducers which are disposed diametrically opposite each other with reference to the body of fibrous material in the bore 644, and the monitoring devices 648b, 648d constitute a second pair of photoelectronic transducers which are also disposed diametrically opposite each other. The monitoring devices alternate with the radiation sources in the circumferential direction of the body of fibrous material. The purpose of such distribution of radiation sources and monitoring devices is to ensure that the monitoring devices are in a position to generate signals which are indicative of one or more characteristics of radiation which has penetrated through a certain portion of the body of fibrous material and has been reflected and/or scattered by the particles of fibrous material in the body In other words, the monitoring devices 648a–648d do not monitor radiation which has invariably or necessarily passed diametrically across the entire body of fibrous material in the bore 644 but rather the radiation which has been reflected or scattered subsequent to its penetration into the fibrous material. Such mode of ascertaining the density of the body of fibrous material exhibits the advantage that the amount of radiation which reaches the monitoring devices is incomparably greater than the amount of radiation which reaches the monitoring devices 48a–48c in the apparatus of FIGS. 2 and 3. Based on the results of experiments, the amount of radiation which reaches the monitoring devices 648a–648d in the apparatus of FIG. 6 is in the range of ten times the amount of radiation reaching the monitoring devices 48a–48c of the apparatus which are shown in FIGS. 2 and 3.

In order to ensure that the results of measurements cannot be distorted by radiation which issues from the sources 647a–647d and is reflected at the exterior of the body of fibrous material in the bore 644 (i.e., by radiation which has not as yet penetrated into such body), the apparatus of FIG. 6 preferably further comprises means for intercepting such reflected radiation. The intercepting means includes light traps which are disposed between the inner ends of neighboring radial bores 81. The illustrated light traps include axially parallel recesses or grooves 83 which are machined into or are otherwise formed in the internal surface of the sleeve 643. The surfaces bounding the grooves 83 are coated with a black pigment or the like so as to reliably absorb and thus prevent reflection toward the monitoring devices 648a–648d of that radiation which issues from the sources 647a–647d and is reflected by the exterior of the body of fibrous material in the bore 644, i.e., which does not penetrate into the body of fibrous material. The percentage of radiation which is reflected by the exterior of the tubular wrapper of a tobacco filler can be quite substantial.

The apparatus of FIG. 6 has four radiation sources and four monitoring devices. The number of radiation sources and/or monitoring devices can be increased above or reduced to less than four. For example, the apparatus can comprise a single pair of radiation sources (647a, 647c or 647b, 647d) which are disposed diametrically opposite each other and the two pairs of monitoring devices 648a to 648d. Alternatively, the apparatus of FIG. 6 can comprise a single pair of radiation sources (e.g., the sources 647a, 647c) and each of the other six radial bores 81 can contain a discrete monitoring device. It will be seen that the number of radiation sources may but need not match the number of monitoring devices. All that counts in the apparatus of FIG. 6 is to ensure that the radiation sources and the monitoring devices are not installed diametrically opposite each other to thus guarantee that each monitoring device is located in the path of radiation which is reflected and/or scattered subsequent to penetration of such radiation into the body of fibrous material.

The apparatus of FIG. 6 exhibits the aforediscussed advantage that the amount of radiation which has passed through a portion at least of the body of fibrous material prior to impinging upon a monitoring device is much greater than in the apparatus of FIGS. 2 and 3. Another advantage of the apparatus 629 is that the monitoring devices are not directly irradiated by the radiation sources in the absence of a body of fibrous material in the bore 644. Direct irradiation of highly sensitive photoelectronic transducers could lead to the development of drift phenomena which could affect the accuracy of the testing operation, at least during the interval immediately following readmission of a body of fibrous material into the sleeve 643.

Figure 7:
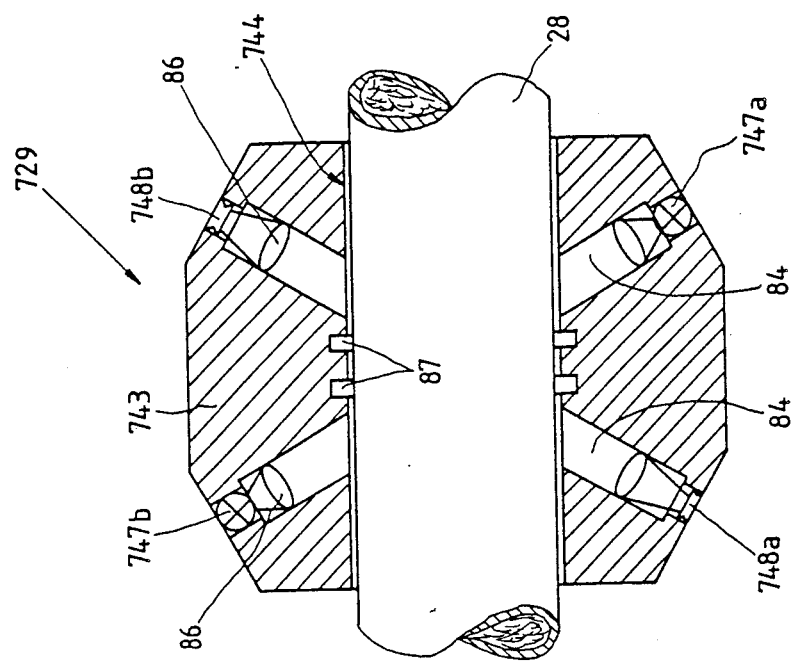
FIG. 7 is an enlarged fragmentary longitudinal sectional view of an additional density measuring apparatus.

The density measuring apparatus 729 of FIG. 7 comprises a sleeve 743 with an axial bore or hole 744 for a wrapped filler 28 of tobacco and/or other fibrous material of the tobacco processing industry. The sleeve 743 has additional bores or holes 84 which communicate with the bore 744 and whose axes are inclined with reference to the longitudinal direction of the wrapped filler 28, i.e., the axes of the bores 84 are located in a plane which is not normal to but rather includes the axis of the bore 744. Two of the bores 84 contain radiation sources 747a, 747b which are disposed substantially diametrically opposite each other with reference to the wrapped filler 28, and the other two bores 84 contain monitoring devices 748a, 748b which are also disposed diametrically opposite each other. The arrangement is such that radiation which issues from the source 747a and is reflected and/or scattered by fibrous material within the tubular envelope of the wrapped filler 28 is directed into the bore 84 for the monitoring device 748a, and that radiation which issues from the source 747b and is reflected and/or scattered by fibrous material in the envelope of the wrapped filler 28 is directed toward the monitoring device 748b. The bores 84 further contain lenses 86 and/or other suitable optical elements to ensure proper propagation of radiation from the sources 747a, 747b and into the monitoring devices 748a, 748b. Radiation intercepting means in the form of groove-like traps 87 are disposed between the bores 84 for the radiation sources and the bores 84 for the monitoring means. Each of the grooves 87 can constitute a circumferentially complete groove which is machined into or otherwise formed in the internal surface of the sleeve 743 between the bores 84 for 747a, 748b on the one hand and the bores 84 for 747b, 748a on the other hand. These traps intercept radiation which is reflected by the tubular envelope of the filler 28.

The advantages of the density measuring apparatus 729 are identical with those of the apparatus of 629 of FIG. 6. Thus, the monitoring devices 748a, 748b receive larger quantities of radiation which has passed at least through a portion of fibrous material in the wrapper of the filler 28, and these monitoring devices are not directly irradiated by the sources 747a, 747b when the axial bore 744 of the sleeve 743 is empty.

FIGS. 8 and 9 illustrate a further density measuring apparatus 829 which can be used in a cigarette maker or in a filter rod maker to monitor the density of an unwrapped body or stream 91 of fibrous material (e.g., tobacco). The means for transporting the stream 91 longitudinally includes a tobacco channel 16 constituting a means for guiding the stream along a predetermined path which is defined by two sidewalls 88 and by one elongated reach or stretch of an endless foraminous belt conveyor 17 travelling along one side of a perforated wall 89 forming part of a stationary suction chamber 18 and being integral with the sidewalls 18a of the suction chamber. The sidewalls 88 have elongated portions 92 which are disposed opposite each other and flank a portion of the path for the tobacco stream 91. The portions 92 transmit radiation in the visible, ultraviolet or infrared range of the spectrum, depending on the nature of composite radiation sources 93, 94 which are used in the density measuring apparatus 829. The wall 89 of the suction chamber 18 has perforations 90 which enable the foraminous belt conveyor 17 to attract the stream 91 in the space between the sidewalls 88 of the tobacco guiding means.

The composite radiation source 93 includes four discrete sources 93a, 93b, 93c, 93d which are spaced apart from one another, as considered transversely of the stream 91, and the same applies for the discrete sources (not specifically shown) of the composite source 95. The composite monitoring means 96 of the density measuring apparatus 829 comprises a row of four discrete monitoring devices 96a, 96b, 96c, 96d which are disposed at different distances from the belt conveyor 17, and the same applies for the four discrete monitoring devices (not specifically shown) of the composite monitoring means (95). The directions in which the discrete radiation sources 93a–93d and the discrete radiation sources of the composite source 94 emit radiation are inclined with reference to the longitudinal direction of the stream 91, and each discrete source of the composite source 93 is located substantially diametrically opposite a discrete source of the composite source 94 This also holds true for the discrete monitoring devices of the monitoring means 95 and the discrete monitoring devices of the monitoring means 96 In other words, none of the discrete monitoring devices are directly exposed to radiation issuing from the radiation sources when the channel 16 is empty. The discrete monitoring devices receive radiation which is reflected and/or scattered by the fibrous material of the stream 91 when the density measuring apparatus 829 is in use. This apparatus exhibits the advantage that it can ascertain the density of several strata of the stream 91, i.e., the density of several layers which are parallel with the axis of the stream.

The apparatus 629, 729 and 829 can be used with equal or similar advantage to monitor the density of a stream or filler of fibrous filter material. Moreover, the apparatus 829 can be used with equal or similar advantage to monitor the density of fibrous material in a wrapped tobacco filler.

It has been found that the entirely harmless photocells which operate with infrared light can ensure highly accurate monitoring of the density of successive increments of the filler in the cigarette rod 28. Similar apparatus can be used with equal advantage for measuring the density of other bodies of fibrous material, e.g , streams of fillers which contain tobacco particles and filter material for tobacco smoke or which contain only filter material. The tubular wrapper which surrounds the filler of the cigarette rod 28 does not interfere with accurate determination of density.

The utilization of one or more sources of infrared radiation is preferred at this time. However, it is equally within the purview of the invention to utilize one or more sources of visible or ultraviolet light. It has been ascertained that the results of testing with visible and ultraviolet light are also quite satisfactory. The apparatus for testing with visible light or ultraviolet light are or can be identical with the aforediscussed apparatus for testing with one or more sources of infrared radiation. Therefore, the drawing does not specifically show the apparatus wherein the sources of infrared radiation are replaced with suitable sources of visible or ultraviolet light.

An important advantage of the improved method and apparatus is that there is no need to employ sources of beta rays, X-rays or other radioactive radiation which necessitates numerous complex and expensive undertakings in order to ensure that the plant will be approved by the authorities and that the attendants will be adequately protected. The improved method and apparatus are based on the recognition that infrared rays, ultraviolet rays or even visible rays are capable of penetrating through a body of fibrous material and that the intensity and/or other characteristics of such radiation can be ascertained with a requisite degree of accuracy after their emergence from the body so that the signals which are generated by the monitoring means accurately reflect the density of the corresponding portion or portions of the body. One would have expected that the long-wavelength visible and infrared radiation would be absorbed by the fibrous material and/or that an excessively high percentage of such radiation would be reflected by the wrapper or by the exterior of an unwrapped body of fibrous material so that the results of measurements would be unsatisfactory. Quite surprisingly, the results of tests indicate unequivocally that the measurement is highly accurate, especially if the apparatus employs two or more photocells, i.e., if selected portions of the stream or filler are at least partially traversed by two or more mutually inclined beams of infrared radiation, ultraviolet radiation or visible light (with a wavelength between 150 and 15,000 nm). The signals which are generated by two or more transducers are then processed into a single signal which is indicative of average density of the corresponding portion of the body of fibrous material.

The placing of discrete photocells one after the other, as considered in the direction of advancement of the body of fibrous material (e.g., in a manner as shown in FIG. 2), and the transmission of signals from consecutive transducers at intervals whose duration is a function of the speed of the body of fibrous material is desirable and advantageous when the speed of the body varies. Such distribution of the photocells and such sequencing of the transmission of signals from the transducers results in the generation of highly reliable averaged density signals which can be used to control the trimming device and/or other parts of the machine or production line in which the improved apparatus is put to use.

The purpose of the additional transducer or transducers which generate reference signals is to eliminate the undesirable influence of drift phenomena and/or contamination of photocells in actual use. Such drift phenomena and/or contamination of photocells entails fluctuations of intensity of radiation which is caused to penetrate through the rod 28. The beam of radiation which impinges upon the transducer of the source of reference signals bypasses the interior of the rod 28, either entirely or in part. Alternatively, and as described in connection with FIG. 2, the beam of radiation which impinges upon the transducer 54 of the means for influencing the sources of radiation can be caused to impinge upon and to be reflected (at least in part) by the wrapper or by the exterior of an unwrapped stream so that the transducer 54 generates signals which are indicative of one or more characteristics of reflected ultraviolet, infrared or visible light. The additional photocell may but need not always be mounted in the sleeve, as long as at least a portion of radiation issuing from its source does not traverse the filler of the rod 28. The signals from the transducer or transducers of the additional photocell or photocells can be used to influence the regulator 57 in a sense to ensure that the intensity of radiation issuing from the sources (such as 47a–47c) remains constant and/or the transducer or transducers (54, 52b) can be used to transmit signals to the evaluating circuit 51 so that the latter is enabled to modify the averaged density signal in dependency on the characteristics of the signal or signals from the source or sources of reference signals, i e , in dependency on deviations of the intensity of beams which are emitted by the sources (such as 47a–47c) from an optimum value.

Certain prior proposals involve the testing of wrapped or unwrapped fillers of tobacco or the like with optical means. Reference may be had for example, to British patent applications Nos. 2,149,101, 2,149,099 and 2,140,915 as well as to German Offenlegungsschrift No. 34 37 753. These prior publications disclose optical photocells for monitoring the external surface of the filler. Monitoring of the external surfaces of unwrapped bodies of fibrous material is disclosed in U.S. Pat. Nos. 4,284,087, 4,423,742 and 4,280,516. However, none of the measurements which are carried out by the apparatus of the just enumerated patents and patent applications are indicative of the density of the filler. The same applies for apparatus which are used to test a composite rod of filter material with beams of visible light in order to ascertain the positions and the length of portions containing different filter materials. Such apparatus are used for detection of defective portions of filter rods, e.g., for detection of undesirable gaps between neighboring filter plugs. Reference may be had to U.S. Pat. Nos. 4,238,994, 4,212,541 and 4,001,579.

Filter materials, especially cellulose acetate fibers which are normally used for the making of filter mouthpieces absorb relatively small quantities of visible light so that, if visible light is used for the testing of a filter rod which comprises sections containing different types of filter material which absorb larger or smaller quantities of visible light, it is possible to determine the locations where filter rod sections exhibiting pronouncedly different properties (as regards the absorption of visible light) (can be readily ascertained) with photocells which employ sources of visible light. On the other hand, tobacco absorbs greater quantities of visible light than filter material so that a monitoring of the density of a filler of tobacco particles (such filler normally contains highly compacted tobacco) with ultraviolet, visible or infrared light was considered to constitute an exercise in futility. This is the reason that the art of which applicants are aware at this time does not contain any proposals to use such light in connection with monitoring of the density of a wrapped filler or an unwrapped stream of tobacco or like fibrous material, especially in a cigarette maker or in an analogous machine for the making of rod-shaped smokers' products wherein it is highly desirable and actually necessary to detect all, even minute, deviations of actual density of the filler or stream from an optimum density.

British Pat. No. 1,320,151 discloses a photocell which is used to monitor the mutual spacing of cigarettes which form a file and are caused to advance axially. German Pat. No. 701,052 discloses a distributor which is used in a cigarette maker and employs a plurality of photocells serving to ascertain the density of a tobacco shower or carpet. The density of a shower or carpet of tobacco in the distributor of a cigarette maker is low or very low since the purpose of the distributor is to spread out the particles and to separate interlaced tobacco shreds so as to allow for subsequent formation of a homogeneous tobacco stream. Therefore, the monitoring of density of a shower of tobacco particles with visible light was deemed to be much more likely to furnish acceptable results than the monitoring of a dense stream or a highly compacted filler of wrapped tobacco particles or similar fibrous material. Nevertheless, the proposal in German Pat. No. 701,052 failed to gain acceptance in the tobacco processing industry. At any rate, the teaching of this German patent does not suggest the utilization of ultraviolet, infrared or visible radiation in apparatus for measuring, with a high or extremely high degree of accuracy, the density of a stream or a wrapped filler which consists of or contains particles of tobacco.

The results of experiments with the improved density monitoring apparatus are highly satisfactory. As mentioned above, the results are especially satisfactory (i.e., highly accurate) if the apparatus employs several photocells each of which is arranged to emit a beam of light, especially infrared light, at a certain angle with reference to the other beam or beams (e.g , at angles of 120 degrees, as considered in the circumferential direction of the cylindrical wrapper of a wrapped tobacco filler rod). The improved apparatus is simpler, less expensive and safer than heretofore known apparatus which measure the density of a wrapped tobacco filler with beta rays, X-rays or other sources of corpuscular radiation The same applies for the evaluating circuit and other components of the improved apparatus.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

I claim:

1. Apparatus for ascertaining the density of an elongated body of fibrous material, comprising a source of electromagnetic radiation with a wavelength in one of the ultraviolet, visible and infrared ranges of the spectrum including means for directing at least one beam of such radiation into the body of fibrous material in at least on predetermined direction at least substantially at right angles to the longitudinal direction of the elongated body so that the beam penetrates through at least a portion of the body and at least one of its characteristics is influenced by the density of the body, at least some of the radiation being reflected and scattered by the fibrous material of the body so that the direction of propagation of reflected and scattered radiation departs form said at least one predetermined direction and such reflected and scattered radiation emerges from the body in at least one second direction other than said at least one predetermined direction; and means for monitoring the characteristic of at least some of the scattered and reflected radiation subsequent to its emergence from the body of fibrous material in said at least one second direction, said monitoring means being oriented to monitor radiation which is scattered and reflected substantially transversely of said at least one predetermined direction and substantially at right angles to the longitudinal direction of said elongated body, said monitoring means including means for generating a signal which is indicative of the monitored characteristic of the radiation.

2. A method of ascertaining the density of an unwrapped stream which contains particles of tobacco, comprising the steps of transporting the stream along a predetermined path in a cigarette maker; guiding the stream in a portion of said path within an open-sided channel; directing at least one beam of electromagnetic radiation with a wavelength in one of the visible and infrared ranges of the spectrum into the stream of fibrous material so that the beam penetrates through the channel and through at least a portion of the stream and at least one of its characteristics is influenced by the density of such stream; monitoring the one characteristic of the beam subsequent to its penetration through at least a portion of the stream of fibrous material; and generating a signal which is indicative of the monitored characteristic of the beam.

* * * * *

UNITED STATES PATENT AND TRADEMARK OFFICE
CERTIFICATE OF CORRECTION

PATENT NO. : 4,986,285
DATED : January 22, 1991
INVENTOR(S) : Andrzej RADZIO et al.

It is certified that error appears in the above-indentified patent and that said Letters Patent is hereby corrected as shown below:

On the title page:
[75] INVENTORS: "Stems" should read --Siems--.

Signed and Sealed this

Fourth Day of January, 1994

Attest:

BRUCE LEHMAN

Attesting Officer         Commissioner of Patents and Trademarks